US00PP34184P2

(12) United States Plant Patent
Bradford et al.

(10) Patent No.: US PP34,184 P2
(45) Date of Patent: May 3, 2022

(54) NECTARINE TREE NAMED 'PEARLICIOUS VIII'

(50) Latin Name: *Prunus persica*
Varietal Denomination: Pearlicious VIII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,910

(22) Filed: Dec. 17, 2021

(51) Int. Cl.
*A01H 6/74* (2018.01)
*A01H 5/08* (2018.01)

(52) U.S. Cl.
USPC ..... Plt./188

(58) Field of Classification Search
USPC ..... Plt./188
See application file for complete search history.

(56) References Cited

U.S. PATENT DOCUMENTS

PP18,715 P2 4/2008 Bradford
PP22,471 P2 1/2012 Bradford
PP23,607 P2 5/2013 Bradford

*Primary Examiner* — Annette H Para

(57) ABSTRACT

The present invention relates to a new and distinct variety of nectarine tree, *Prunus persica*, broadly characterized by a large size, vigorous, hardy, self-fertile, productive and regular bearing tree. The variety blooms during the mid season and requires about 525 chilling hours. The fruit matures under the ecological conditions described in late June, with first picking on Jun. 26, 2021. The fruit is uniform, large in size, oblate in shape, clingstone in type, firm in texture, white in flesh color, full red in skin color, a tasty blend of low acid and high sugar in flavor, and has a bitter tasting kernel. The fruit has a very long harvest window, as it can hang firm on the tree for up to 3 weeks.

1 Drawing Sheet

Botanical classification: *Prunus persica.*
Variety denomination: 'PEARLICIOUS VIII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Pearlicious VIII'.

In 2014 we made a first generation hybridization using 'Pearlicious VI' (U.S. Plant Pat. No. 23,607) nectarine as the selected seed parent and 'Kay Diamond VII' (U.S. Plant Pat. No. 18,715) nectarine as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2018 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Pearlicious VI' (U.S. Plant Pat. No. 23,607) nectarine, by being self-fertile, by blooming in the mid season, by having a large flower, by having a bitter kernel, and by producing nectarines that are white in flesh color, almost full red in skin color, clingstone in type, firm in texture, and low in acid, but is distinguished therefrom by having a larger tree, by having globose instead of reniform leaf glands, and by producing nectarines that are a somewhat larger in size, that are sweeter, that have much less skin freckling, and that have a longer harvest window starting about five days earlier and lasting about a week longer.

The present variety is similar to its pollen parent, 'Kay Diamond VII' (U.S. Plant Pat. No. 18,715) nectarine, by being self-fertile and by producing nectarines that are full red in skin color, clingstone in type, and firm in texture, but is quite distinguished from it by producing nectarines that are white instead of yellow in flesh color, that are lower in acid, that are much sweeter, and that ripen about twenty days later.

The present variety is most similar to 'Pearl Time' (U.S. 22,471) nectarine, by being self-fertile, by blooming in the mid season, by having a large flower, by having globose leaf glands, by having a bitter kernel, and by producing nectarines that are white in flesh color, that are almost full red in skin color, that are firm in texture, that are sweet and lightly acidic in flavor, but is distinguished therefrom by having a larger tree and by producing nectarines that are much larger in size, that have much less skin freckling, that are clingstone instead of semi-freestone in type, that are oblate instead of globose in shape and that mature about 4 days later.

SUMMARY OF VARIETY

In summary, the present nectarine variety is characterized by a large size, vigorous, hardy, self-fertile, productive and regular bearing tree. The variety blooms during the mid season and requires about 525 chilling hours. The fruit matures under the ecological conditions described in late June, with first picking on Jun. 26, 2021. The fruit is uniform, large in size, oblate in shape, clingstone in type, firm in texture, white in flesh color, full red in skin color, a tasty blend of low acid and high sugar in flavor, and has a bitter tasting kernel. The fruit has a very long harvest window, as it can hang firm on the tree for up to 3 weeks.

DRAWING

The accompanying photograph consists of four whole fruits positioned to display the characteristics of the skin color and form, one divided fruit to reveal the flesh and stone, typical leaves, a tip shoot growth, and three insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 8, 2021, on the original tree during its seventh growing season. The blossom and flower descriptions were made the previous blooming season. All major color code designations are by reference to the Inter-Society Color Council, National Bureau of Standards. Common color names are also used occasionally.

PARENTAGE

Seed parent: 'Pearlicious VI' (U.S. Plant Pat. No. 23,607) nectarine.

Pollen parent: 'Kay Diamond VII' (U.S. Plant Pat. No. 18,715) nectarine.

TREE

Size: Large, reaching and maintaining a height of 12' [3.66 m.] and a spread of 12' [3.66 m.] after seven growing seasons utilizing typical dormant pruning.

Vigor: Vigorous, responding about average to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to a vase shape.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Chilling requirement: About 525 hours.

Leaf bud burst: Medium to late, during the end of flowering.

Trunk:

*Size*.—Medium, reaching a maximum diameter of 5½" [139.7 mm.] after the seventh growing season.

*Texture*.—Medium to shaggy.

*Bark color*.—A Light grayish yellowish brown [79. l.gy.yBr] and Light yellowish brown [76. l.yBr] variegation with Brownish gray [64. brGy] crevices present.

*Lenticels*.—Approximate Number Per Square Inch: 10. Color: Strong yellowish brown [74. s.yBr]. Average Size: ⅜" [9.5 mm.] in length. The width is typically one fourth as much as the length. Shape: Elongated.

Branches:

*Size*.—Medium, diameter of main scaffold is 2¾" [69.9 mm.] measured 12" above the crotch, diameter of limb is 1⅜" [34.9 mm.] measured 12" above the first fork.

*Texture*.—Smooth to medium on first and second year wood, increasing in roughness with age.

*Color*.—1st Year Wood Topside: Grayish red [19. gy.R]. 1st Year Wood Underside: Brilliant yellow green [116. brill.YG]. Older Wood: A Brownish [54. brO] and Strong brown [55. s.Br] variegation with Dark grayish brown [62. d.gy.Br] crevices present.

*Lenticels*.—Number Per Square Inch: About 35 on second year wood. Color: Dark orange yellow [72. dOY]. Average Size: Medium, 1/16" [1.6 mm.] in length. The width is typically one fourth as much as the length. Shape: Elongated.

Leaves:

*Size*.—Large. Average Length: 7 5/16" [185.7 mm.]. Average Width: 1 15/16" [49.2 mm.].

*Arrangement*.—Alternate.

*Thickness*.—Medium.

*Form*.—Elliptical.

*Apex*.—Acuminate.

*Base*.—Acute, with an average base angle of 75 degrees.

*Surface*.—Smooth on both sides.

*Color*.—Dorsal Surface: Moderate olive green [125. m.OlG]. Ventral Surface: Moderate yellow green [120. m.YG].

*Red midvein*.—Absent.

*Margin*.—Finely serrate.

*Venation*.—Pinnately net veined.

*Petiole*.—Average Length: ½" [12.7 mm.]. Average Thickness: 1/16" [1.6 mm.]. Color: Moderate olive green [125. m.OlG].

*Stipules*.—Number: 2 per leaf, up to 6 per growing Lip. Average Length: ¼" [6.4 mm.]. Color: Brilliant yellow green [116. brill.YG] becoming Grayish red [19. gy.R] with age.

*Glands*.—Number: 2 to 4 per leaf. Position: Very slightly alternate, first pair is located at the intersection of petiole and base of blade. Form: Globose. Size: Medium, about 1/32" [0.8 mm.] in diameter. Color: Moderate yellow green [120. m.YG] becoming Deep reddish brown [41. deep rBr] with age.

*Leaf buds*.—Pointed.

Flower buds:

*Hardiness*.—Hardy, with respect to central California blooming season.

*Diameter*.—Typically ⅜" [9.5 mm.] 1 week before bloom.

*Length*.—Typically ⅝" [15.9 mm.] 1 week before bloom.

*Form*.—Not appressed.

*Surface*.—Pubescent.

*Tip color*.—Pale pink [7. p.Pk].

Flowers: Perfect, complete, perigynous, usually a single pistil, about thirty stamens, five sepal and petal locations alternately positioned.

*Type*.—Showy, large.

*Average flower diameter*.—1 13/16" [46.0 mm.].

*Average flower depth*.—½" [12.7 mm.] when fully open.

*Number of petals*.—Five, extra petal fragments very common, double blossoms occasionally observed.

*Petal arrangement*.—Overlapping.

*Petal shape*.—Circular to oval.

*Petal margin*.—Entire, slightly wavy.

*Average petal diameter*.—¾" [19.1 mm.].

*Average petal length*.—¾" [19.1 mm.].

*Petal apex*.—Rounded.

*Petal base*.—Rounded.

*Petal color*.—Pale pink [7. p.Pk] on both sides.

*Anthocyanin coloration intensity*.—Weak.

*Anther color*.—Moderate reddish orange [37. m.rO] surrounding a Light yellow [86. l.Y] center at bloom onset.

*Pollen*.—Anthers produce an abundance of Brilliant yellow [83. brill.Y] pollen.

*Stigma color*.—Light greenish yellow [101. l.gY].

*Stigma position*.—Typically located slightly above the nearby anthers.

*Stamen position*.—Typically located about 1/16" [1.6 mm] below the petals.

*Average pistil length*.—13/16" [20.6 mm.].

*Average stamen length*.—9/16" [14.3 mm.].

*Ovary*.—Non-pubescent.

*Sepal color*.—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.

*Sepal length*.—⅜" [9.5 mm.].

*Sepal width*.—5/16" [7.9 mm.].

*Sepal apex*.—Rounded to elliptical to match the sepal length and width.

*Sepal margin*.—Fairly smooth.

*Sepal outer surface*.—Pubescent.

*Fragrance*.—Moderate.

*Blooming period*.—Medium, blooms at the same time as 'Majestic Pearl' (U.S. Plant Pat. No. 18,778) nectarine.

*Onset of bloom*.—One percent on Feb. 19, 2021.

*Date of full bloom*.—Mar. 3, 2021.

*Duration of bloom*.—One to two weeks, dependent on ambient temperature.

*Bloom density*.—Medium to heavy.

*Number per cluster*.—1 to 3 with single flowers most common.

FRUIT

Maturity when described: Firm ripe, Jul. 8, 2021.

Date of first picking: Jun. 26, 2021.

Date of last picking: Jul. 16, 2021.

Size: Uniform, large.

*Average diameter axially*.—2⅞" [73.0 mm.].

*Average diameter across suture plane*.—3⅜" [85.7 mm.].

*Average diameter across cheek plane*.—3⅜" [85.7 mm.].

*Typical weight*.—10.9 ounces [310 grams].

Form: Uniform, oblate, symmetrical.

*Longitudinal section form*.—Oblate.

*Axial view*.—Round.

Suture: A shallow groove extending from the base, along the side, and ending about ½" [12.7 mm.] beyond the pistil point.

*Near the base*.—A shallow groove.

*Along the side*.—A shallow trough.

*Near the apex*.—A shallow groove.

Ventral surface: Rounded, lipped on both sides.

Lips: Fairly equal.

Cavity: Flaring, Pale yellow green [121. p.YG] stem markings present.

*Depth*.—½" [12.7 mm.].

*Breadth*.—1⅝" [41.3 mm.].

Base: Truncate.

Apex: Truncate, somewhat cordate when viewed parallel to the suture.

Pistil point: Negligible in length, depressed within the suture.

Stem: Medium.

*Average length*.—⅜" [9.5 mm.].

*Average width*.—3/16" [4.8 mm.].

Skin:

*Thickness*.—Medium.

*Surface*.—Smooth.

*Tenacity*.—Tenacious to the flesh.

*Astringency*.—Non-astringent.

*Tendency to crack*.—Slight.

*Color*.—Vivid deep red [14. v.deep R] over a Deep red [13. deep R] background with very minor Pale yellow [89. p.Y] freckling toward the apex.

Flesh:

*Color*.—Yellowish white [92. yWhite) with Moderate red [15. m.R] streaking near the stone and toward the skin on the suture side.

*Surface of pit cavity*.—Covered with a blend of Moderate red [15. m.R] and Yellowish white [92. yWhite) broken fibers when twisted away from the stone.

*Amygdalin*.—Scarce.

*Juice*.—Moderate, rich.

*Texture*.—Firm, crisp.

*Fibers*.—Fine, tender.

*Ripens*.—Fairly even.

*Flavor*.—A tasty blend of slight acid and strong sugar, very sweet, typically 18-22 brix.

*Aroma*.—Slight.

*Eating quality*.—Excellent.

STONE

Type: Clingstone.
Form: Oval.
Hilum: Narrow, oval.
Base: Rounded.
Apex: Rounded to truncate.
Sides: Fairly equal.
Tip: Negligible.
Surface: Irregularly furrowed toward the apex, pitted toward the base.
Ridges: Jagged.
External color: Deep yellowish brown [75. deep yBr] when first removed.
Pit wall color when cracked: Moderate brown [58. m.Br].
Cavity surface color: Strong yellowish brown [74. s.yBr].
Average pit wall thickness: 3/16" [4.8 mm.].
Average length: 1¼" [31.8 mm.].
Average width: 1⅛" [28.6 mm.].
Average breadth: ⅞" [22.2 mm.].
Tendency to split: None observed.
Kernel:
*Form*.—Oval.
*Skin color*.—Pale yellow [89. p.Y].
*Pellicle color*.—Dark brown [59. d.Br].
*Vein color*.—Light brown [57. l.Br].
*Taste*.—Bitter.
*Viable*.—Yes.
*Average length*.—¾" [19.1 mm.].
*Average width*.—9/16" [14.3 mm.].
*Amygdalin*.—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described.

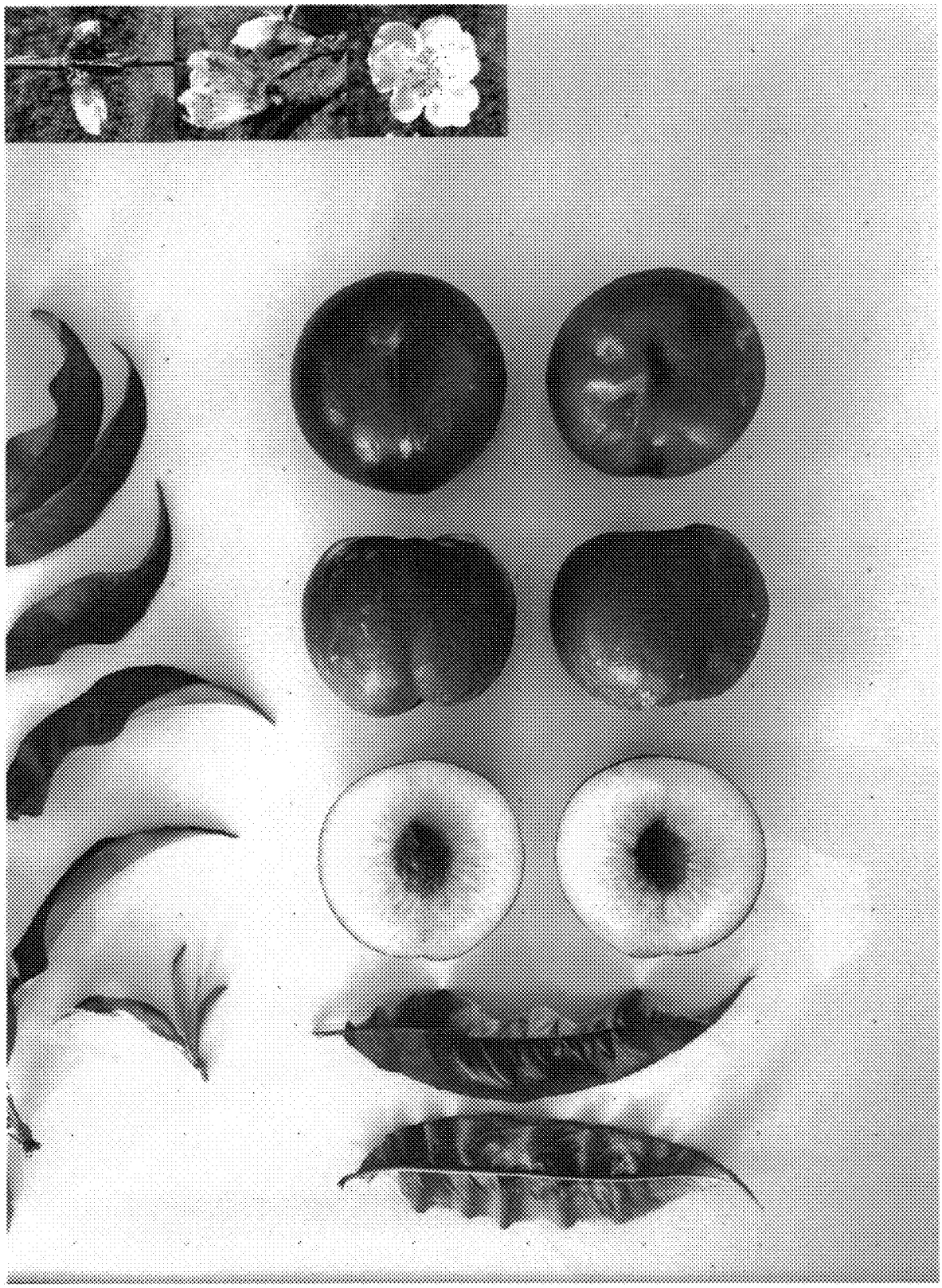

* * * * *